United States Patent [19]

Falk et al.

[11] 4,318,614
[45] Mar. 9, 1982

[54] EMISSION SPECTRAL ANALYSIS DEVICE

[75] Inventors: Heinz Falk, Berlin; Erwin Hoffman, Hohenneuendorf; Christian Lüdke, Berlin, all of German Democratic Rep.

[73] Assignee: Jenoptik Jena GmbH, Jena, German Democratic Rep.

[21] Appl. No.: 143,573

[22] Filed: Apr. 25, 1980

[30] Foreign Application Priority Data

May 3, 1979 [DD] German Democratic Rep. ... 212628

[51] Int. Cl.$^3$ .......................................... G01N 21/71
[52] U.S. Cl. .................................... 356/311; 356/312
[58] Field of Search ..................... 356/311, 312, 314; 313/209, 210

[56] References Cited

PUBLICATIONS

Woodruff et al., *Applied Spectroscopy*, vol. 22, No. 4, Jul.-Aug. 1968 pp. 348 and 349.
Menge et al., *Messtechnik*, vol. 80, Oct. 1972, pp. 304-306.

*Primary Examiner*—F. L. Evans
*Attorney, Agent, or Firm*—Jordan and Hamburg

[57] ABSTRACT

In a device for the emission spectral analysis of samples, including an evaporating tube for receiving and thermally evaporating a sample, and a hollow cathode and anode for athermally exciting the evaporated sample, the evaporation tube forms said cathode. The anode and cathode are mounted adjacent one another in spaced apart relationship along the axis of the tube.

5 Claims, 1 Drawing Figure

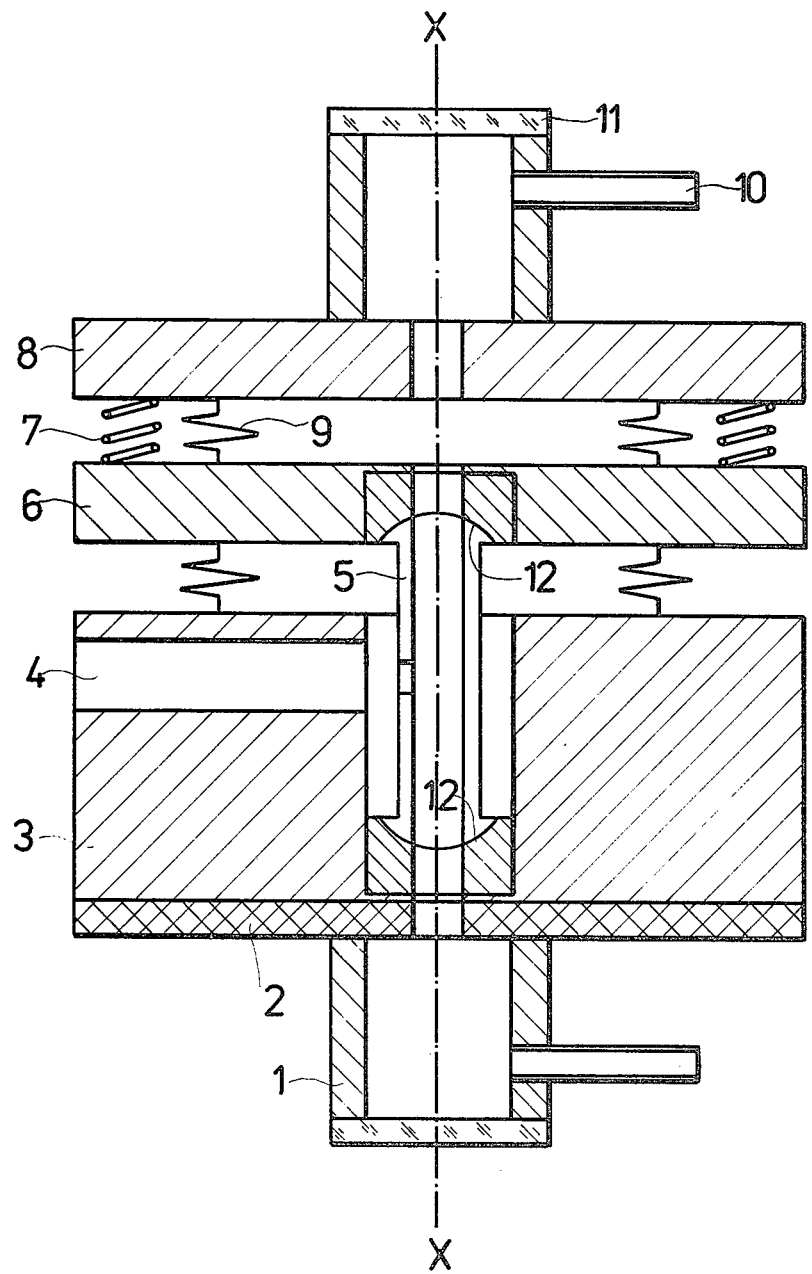

EMISSION SPECTRAL ANALYSIS DEVICE

BACKGROUND OF THE INVENTION

This invention relates to a device for emission spectral analysis, particularly for microprobes, comprising an evaporation tube for receiving and thermally evaporating a sample, as well as a hollow cathode and an anode for the athermal excitation of the evaporated sample. It is useful for the emission spectral analysis of trace elements in small samples in an inert gas.

Conventional hollow cathode lamps for emission spectral analysis use the discharge in a hollow cathode simultaneously for the evaporation of the sample and for the excitation of the atoms of the vapor of the sample. This coupling of the evaporation process and the excitation process renders it impossible to attain optimal conditions for each individual process.

In order to alleviate this problem, a hollow cathode lamp for emission spectral analysis, as disclosed in DD No. 63897 has a cathode block with a heatable evaporation container having an inner space connected to the hollow cathode by a feedpipe. The hollow cathode is provided with a heating system, independent of the heating system for the evaporating container. In this device the analysis sample is first evaporated thermally, and the vapors of the sample are subsequently excited by the discharge of the hollow cathode. This hollow cathode lamp is particularly suitable for the analysis of larger samples (milligram to gram range) because a direct reciprocal effect of the flow discharge with the sample is prevented. When analyzing very small amounts of samples (in the microgram range) only a small part of the total sample vapor is present inside of the excitation space. A diffusion dependent time constant arises in passing the sample vapors from the evaporation vessel to the excitation space. In addition, chemical reactions may occur with the wall of the evaporation vessel. Both of these influences diminish the potential concentration of the sample vapors within the excitation space, and thereby reduce the capability of analyzing the sample, particularly when small amounts of samples are to be analyzed.

An arrangement useful for emission spectroscopy in inert gases is disclosed in DD Nos. 91,574 and 103,321, wherein a unipotential tube is arranged within a heating and evaporation tube, and a grid tube, serving as an anode, is arranged in the unipotential tube. The sample to be evaporated is positioned within this grid-tube. The evaporation tube heats the sample by way of the unipotential tube and the grid-tube. In the arrangement, however, the temperature flow for drying, ashing and evaporation for each sample is too time consuming and lacks definition. It is very difficult to prepare a grid-tube, and its life is subject to many limitations. The sample is excited by a low-pressure discharge occurring between the cathode and the anode, extending through the grid-tube towards the sample. The physical size of the device, as determined by the three concentric tubes, results in a relatively low volume intensity of radiation when the sample is excited.

The invention is directed to the provision of a device for emission spectral analysis, particularly for handling small samples. It avoids direct reciprocal effect of the exciting gas dishcarge with the sample, while guaranteeing a high concentration of the sample vapors within the excitation space. In accordance with the invention, this is achieved by arranging the evaporation tube and the anode axially adjacent one another and spaced apart, and by forming the evaporation tube as a hollow cathode. This guarantees that thermal evaporation and a thermal excitation of the sample occur as processes which are independent of each other, but occur within the same space. The athermal excitation is suitably realized by a discharge in the hollow cathode. The cylindrical evaporation tube may, for example, be graphite, and defines an evaporation and excitation space.

In an advantageous embodiment of the invention, the ends of the evaporation tube are held by spherical cups, one of which is supported by springs. A gas circulation system is provided in order to prevent smudging of the optical windows. According to the invention, dry residues or solid samples are directly excited within the evaporation space of the radiation source, because of the hollow cathode discharge therein. In order that the entire sample be present at the same time within the excitation space as quantitatively as possible, the invention enables the heating to occur so fast that the evaporation time is less than or equal to the time required for diffusion. The device is filled with the gas needed for the discharge of the hollow cathode, and the discharge is fired prior to evaporating the sample.

BRIEF DESCRIPTION OF THE DRAWING

In order that the invention will be more clearly understood, it will now be disclosed in greater detail with reference to the single FIGURE of the accompanying drawing, which is a cross-sectional view of an emission spectral analysis device in accordance with the invention.

DETAILED DESCRIPTION OF THE INVENTION

Referring now to the drawing, the evaporation and excitation space of the device is formed by the graphite cylindrical heating and evaporation tube 5. This heating tube 5 is held at its ends by spherical cups 12 in order to ensure positive gripping. The heating potential for the heating tube 5 is applied by way of block 3 and plate 6. Springs 7 and movable plate 6 guarantee that the heating tube 5 may change its length with temperature changes without interrupting the electrical contacts. Elastic elements 9 serve as vacuum seals and also as electrical insulation between the block 3 and plate 6. The sample is introduced by way of a vacuum-lock (not shown) through a borehole 4 in the block 3, and thence into the heating tube 5, for instance by the use of a micropipet. The production of the discharge in the hollow cathode, required for the excitation, is actuated by connecting tube 1 as a hollow anode and element 5 as the cathode of the device. This is the reason that an electrical insulating sheet 2 is disposed between anode 1 and block 3. Discharge may occur by the use of direct excitation, or by using square wave pulses. The latter method has the advantage of producing signals which are processed easier. Windows 11 are aligned with the axis X—X of the heating tube 5 at the ends of the device. This construction allows the measurement of emission and absorption. The discharge vessel is connected by means of a pipe 10 to a vacuum pump and a system for the circulation of gases (not shown). The latter protects the windows 11 from smudging.

The arrangement according to the invention has many advantages as compared with prior devices. Thus, samples are accessible for the determination of trace elements. Sample vapors share the common evaporation and excitation space, the analysis cannot be disturbed by potential reaction with the walls of the equipment. The arrangement thereby considerably improves the detection sensitivity.

While the invention has been disclosed and described with reference to a single embodiment, it will be apparent that variations and modifications may be made therein. It is therefore intended in the following claims to cover each such variation and modification as falls within the true spirit and scope of the invention.

We claim:

1. A device for emission spectral analysis, comprising a heating potential and a hollow evaporation tube for receiving and thermally evaporating a sample, said evaporation tube comprising a hollow cathode, and an anode, said anode and cathode being connected to athermally excite the evaporated sample, said anode and cathode being mounted adjacent one another in spaced apart relationship along the axis of said tube.

2. The device of claim 1 comprising cups having spherical recesses mounted to support the ends of said evaporation tube.

3. The device of claim 1 further comprising means for circulating gases in said device.

4. The device of claim 1 comprising a cathode block, said evaporation tube having one end mounted in said block, a plate axially spaced from said cathode block for supporting the other end of said evaporation tube, said plate and block having apertures along the axis of said tube, a second plate axially spaced from said first mentioned plate, and spring means depending from said second plate and urging said first mentioned plate against the respective end of said evaporation tube, said anode being axially spaced from said cathode block and comprising a hollow tube.

5. The device of claim 4 further comprising a second hollow tube mounted axially on said second plate, said second plate having an aperture extending into said second hollow tube, window means mounted on the axis on said second hollow tube and anode, and means for evacuating said device by way of said second hollow tube.

* * * * *